(12) United States Patent
Franklin

(10) Patent No.: US 8,986,717 B2
(45) Date of Patent: Mar. 24, 2015

(54) FRAGRANCE-CONTAINING COMPOSITIONS

(75) Inventor: Kevin Ronald Franklin, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 59 days.

(21) Appl. No.: 13/387,558

(22) PCT Filed: Jul. 7, 2010

(86) PCT No.: PCT/EP2010/059736
§ 371 (c)(1),
(2), (4) Date: Jan. 27, 2012

(87) PCT Pub. No.: WO2011/015417
PCT Pub. Date: Feb. 10, 2011

(65) Prior Publication Data
US 2012/0121677 A1 May 17, 2012

(30) Foreign Application Priority Data
Aug. 6, 2009 (EP) ..................................... 09167370

(51) Int. Cl.
- A61K 8/02 (2006.01)
- A61K 8/00 (2006.01)
- A61Q 15/00 (2006.01)
- A61K 8/11 (2006.01)
- A61K 8/65 (2006.01)

(52) U.S. Cl.
CPC . *A61Q 15/00* (2013.01); *A61K 8/11* (2013.01); *A61K 8/65* (2013.01); A61K 2800/412 (2013.01)
USPC ........................................... 424/401; 424/65

(58) Field of Classification Search
None
See application file for complete search history.

(56) References Cited

U.S. PATENT DOCUMENTS

| | | | |
|---|---|---|---|
| 3,516,941 A | 7/1966 | Matson | |
| 3,792,068 A | 2/1974 | Luedders | |
| 5,126,061 A * | 6/1992 | Michael | 510/106 |
| 5,135,747 A | 8/1992 | Faryniarz | |
| 5,861,144 A | 1/1999 | Peterson et al. | |
| 6,045,835 A | 4/2000 | Soper | |
| 6,110,449 A | 8/2000 | Bacon | |
| 6,653,277 B1 | 11/2003 | Golz-Berner | |
| 2003/0087776 A1 | 5/2003 | Heltovics | |
| 2003/0194416 A1 | 10/2003 | Shefer | |
| 2005/0089540 A1 | 4/2005 | Uchiyama | |
| 2005/0112152 A1 | 5/2005 | Popplewell | |
| 2005/0113267 A1 | 5/2005 | Popplewell | |
| 2005/0153135 A1 | 7/2005 | Popplewell | |
| 2007/0036738 A1 * | 2/2007 | Fletcher et al. | 424/65 |
| 2007/0037731 A1 | 2/2007 | Heltovics | |
| 2007/0037732 A1 | 2/2007 | Heltovics | |
| 2008/0031961 A1 | 2/2008 | Cunningham | |
| 2008/0194454 A1 | 8/2008 | Morgan | |
| 2010/0104611 A1 | 4/2010 | Chan | |
| 2010/0104612 A1 | 4/2010 | Cropper | |
| 2010/0104613 A1 | 4/2010 | Chan | |

FOREIGN PATENT DOCUMENTS

| | | | |
|---|---|---|---|
| EP | 0006739 A1 | | 1/1980 |
| EP | 0303461 | * | 2/1989 |
| EP | 0519531 | * | 12/1992 |
| EP | 1719554 A2 | | 11/2006 |
| EP | 1797947 A2 | | 6/2007 |
| WO | WO9730689 | | 8/1997 |
| WO | WO2006/056096 | * | 6/2006 |
| WO | WO2006056096 | * | 6/2006 |
| WO | WO2006056096 A1 | | 6/2006 |
| WO | WO2011015417 A2 | | 2/2011 |

OTHER PUBLICATIONS

ChemSpider "Allyl cyclohexyl propionate", http://www.chemspider.com/Chemical-Structure.10709942.html?rid=725ed846-39ed-454a-84f8-b4909b0b6ad2 , accessed Jul. 8, 2013.*
ChemSpider "Allyl cyclohexyl propionate", http://www.chemspider.com/Chemical-Structure.10709942.html?rid=725ed846-39ed-454a-84f8-b4909b0b6ad2, accessed Jul. 8, 2013.*
PCT International Search Report in PCT application PCT/EP2010/059736 dated Jun. 8, 2009 with Written Opinion.

* cited by examiner

Primary Examiner — Kortney L Klinkel
Assistant Examiner — Melissa Javier
(74) Attorney, Agent, or Firm — Ronald A. Koatz

(57) ABSTRACT

An antiperspirant or deodorant composition comprising i) an antiperspirant or deodorant active, ii) a liquid carrier for the antiperspirant or deodorant active, and iii) fragrance in which the fragrance comprises a mixture of first and second fragrances, respectively (iiia) and (iiib), the first fragrance (iiia) being free from encapsulation and comprising fragrance components having a boiling point of higher than 250° C. at 1 bar pressure in a weight proportion of greater than 65% and the second fragrance (iiib) being encapsulated in a water-insoluble shear-sensitive encapsulating material and comprising fragrance components having a boiling point of greater than 250° C. at 1 bar pressure in a weight proportion of less than 65%.

18 Claims, No Drawings

FRAGRANCE-CONTAINING COMPOSITIONS

The present invention relates to antiperspirant or deodorant compositions comprising a fragrance and in particular to such compositions containing an encapsulated fragrance as well as a fragrance that is not encapsulated, to a process for the manufacture of fragrance-containing compositions and to the non-therapeutic topical application of fragrance-containing compositions to human skin.

Typical antiperspirant or deodorant compositions comprise both a deodorant active and a fragrance. Herein, the term "deodorant active" excludes a material that acts solely by masking a malodour, but includes any material that actively reduces the formation of malodour. Herein, the term "fragrance" may be used interchangeably with the word "perfume".

Antiperspirant or deodorant compositions comprising both an encapsulated fragrance and a deodorant active are known.

U.S. Pat. No. 5,135,747 (Cheesebrough Ponds) discloses deodorant/antiperspirant compositions comprising both an encapsulated and non-encapsulated fragrance.

U.S. Pat. No. 6,110,449 (P&G) discloses antiperspirant compositions that include perfume/cyclodextrin complexes comprising highly volatile perfume materials having a boiling point of less than or equal to 250° C.

U.S. Pat. No. 5,861,144 (P&G) discloses antiperspirant compositions comprising both an encapsulated and non-encapsulated fragrance, both fragrances containing more than 65% by weight of volatile perfume materials having a boiling point of less than 250° C.

WO 97/30689 (P&G) discloses antiperspirant compositions comprising both an encapsulated and non-encapsulated fragrance.

EP 1,719,554 (IFF) discloses personal cleansing and/or cosmetic compositions containing enduring fragrances.

According to a first aspect of the present invention, there is provided an antiperspirant or deodorant composition comprising i) an antiperspirant or deodorant active,
ii) a liquid carrier for the antiperspirant or deodorant active, and
iii) fragrance in which the fragrance comprises a mixture of first and second fragrances, respectively (iiia) and (iiib), the first fragrance (iiia) being free from encapsulation and being rich in fragrance components having a boiling point of higher than 250° C. at 1 bar pressure and the residue of fragrance components having a boiling point of up to 250° C. at 1 bar pressure and the second fragrance (iiib) being encapsulated in a water-insoluble shear-sensitive encapsulating material and being lean in fragrance components having a boiling point of above 250° C. at 1 bar pressure and the residue of fragrance components having a boiling point of up to 250° C. at 1 bar pressure.

Such compositions according to the first aspect of the invention are intended for non-therapeutic topical application to human skin and to be left in place for an extended period of time. By so selecting the choices of fragrance components in the first (non-encapsulated) and second (encapsulated) fragrances, it is possible to achieve a comparatively level perception of fragrance over an extended period of time. In particular, by selecting a non-encapsulated (free) fragrance that is rich in components having a boiling point of above 250° C., the release of fragrance still is a burst, but a burst over an extended period of time compared with a fragrance blend that is rich in components having a boiling point of at or below 250° C. In addition, by selecting a blend that is lean in components having a boiling point of above 250° C. for encapsulation, it is possible for the fragrance that is released from the encapsulated fragrance to be perceived more quickly than if the encapsulated blend were rich in components having a boiling point of above 250° C.

A further benefit of compositions according to the first aspect of the invention is their excellent performance when applied to the underarms or axillae. In this environment, the water-resistance of the encapsulates and their ability to be broken by shear enables the desired fragrance profile to be delivered over an extended period of time. Further, subsequent to the composition being applied to underarms, fragrance release can be triggered by body movement, giving a fragrance boost during exercise, for example, when it most needed.

In a second aspect of the invention, there is provided a process for the preparation of composition according to the first aspect in which a composition comprising the antiperspirant or deodorant active (i), the liquid carrier (ii) and the fragrances (iiia) and (iiib) are mixed together.

In a third aspect, there is provided a method for inhibiting sweating or/and body odour by topical application to human skin of a composition according to the first aspect of the invention. Said method particularly involves leaving the composition on the skin for an extended period of time, such as at least 1 hour and especially at least 4 hours.

In a fourth aspect, there is provided an antiperspirant or deodorant product in which a composition according to the first aspect is accommodated within a dispensing container.

The present invention relates to antiperspirant or deodorant compositions which contain both a free and an encapsulated fragrance, the free (non-encapsulated) fragrance being rich in perfume components having a boiling point of over 250° C., which are sometimes called higher boiling point perfume components. The encapsulated fragrance herein is rich in lower boiling point perfume components and hence lean in higher boiling point perfume components. The term "rich" herein indicates that the proportion of the higher boiling point perfume components in the fragrance is greater than 65% by weight of the total weight of the perfume components. Herein, correspondingly, lean or poor indicates that the fragrance contains less than 65% by weight of the higher boiling point perfume components. Herein, high boiling point or high BP when used in relation to perfume components indicates a boiling point of higher than 250° C. and low boiling point or low BP, correspondingly means components having a boiling point of up to 250° C. For many components, the boiling point can be measured at 1 bar pressure, but for some, a calculated boiling point is needed.

Accordingly, the fragrance combination of the instant invention can be summarized as the non-encapsulated fragrance being high BP rich and the encapsulated fragrance as being high BP lean. Preferably, the non-encapsulated fragrance comprises 70-90% by weight of fragrance components having a boiling point of >250° C. In some desirable embodiments, the non-encapsulated fragrance contains <20% by weight of fragrance components having a boiling point of ≤220° C. and/or >70% of fragrance components having a boiling point of >270° C. Preferably, the encapsulated fragrance contains 35 to 64% by weight of fragrance components having a boiling point of >250° C. In some desirable embodiments, the encapsulated fragrance contains from 15-35% by weight of fragrance components having a boiling point of ≤220° C. and/or 40-75% by weight of fragrance components having a boiling point of ≤270° C.

Desirably, in an alternative way of characterising the invention, the weight proportion of fragrance components having a boiling point of >250° C. (at 1 bar) (high BP) in the non-encapsulated fragrance is at least 10% greater than the weight proportion of fragrance components having a boiling point of >250° C. (at 1 bar) in the encapsulated fragrance. In a number of chosen embodiments, said difference in high BP proportion is at least 15%. Preferably, the invention is characterised by both ways simultaneously, which is to say that not only is the non-encapsulated fragrance higher BP rich and the encapsulated fragrance high BP lean, but also there is a difference in weight proportion of at least 10% high BP between the non-capsulated and encapsulated fragrances.

Invention fragrance compositions according to the present invention, as defined in either way of characterising it, are especially suitable for antiperspirant compositions, and particularly for such that are intended to be left on skin for a period of at least 4 hours, such as from 5 to 24 hours or longer.

The term "encapsulated" herein indicates that the fragrance is entrapped by an encapsulating material that is solid at 25° C., forming capsules, which by virtue of their diameter may alternatively be considered as microcapsules. Said material is advantageously solid at 35° C., and in many highly desirable embodiments remains solid at 50° C. The ability to remain solid at 35° C. or higher minimises the risk of premature de-encapsulation during transportation or storage, especially in hot climates. The encapsulating material may form an outer shell enveloping the fragrance or/and it may comprise a porous particulate mass which holds the fragrance, possibly within voids within the encapsulating material.

The encapsulating material is selected to enable the capsule to release the fragrance when subjected to shear. They are also selected to not release the fragrance when subjected to water. The term "encapsulate" herein when employed means a capsule.

The shear-sensitive nature of the encapsulates means that they can be broken by physical contact such as by impact or abrasion. An alternative term that can be employed for such capsules is friction-sensitive. The shear-sensitive capsules that are water-insoluble are especially desirable for incorporation into leave-on cosmetic products like antiperspirant or deodorant compositions, because the fragrance can be released over an extended period of time by skin onto which the composition has been applied rubbing against clothing or other skin as for example an arm is moved during normal daily activities. Consequently, fragrance can be released at times that are independent of significant sweating events.

It must be noted that fragrance encapsulates in which the encapsulating material is not shear-sensitive may also be present within compositions according to the invention. Similarly, fragrance encapsulates in which the encapsulating material is water-soluble may also be present.

Desirably, the shear-sensitive, water-insoluble capsules comprise at least 40%, especially at least 50% and particularly at least 60% of the total weight of encapsulated fragrance present. In many highly desirable embodiments, at least 80% by weight of fragrance capsules present are shear-sensitive, water-insoluble capsules.

In some embodiments herein, the composition is free from moisture-sensitive encapsulated fragrance. However, in other valuable embodiments, the compositions contain both the moisture sensitive and shear sensitive encapsulated fragrances, such as particularly in a weight ratio to the former to the latter of at least 1 to 20 and/or up to 3:1. In a number of preferred compositions, the weight ratio of moisture sensitive to shear sensitive capsules is at least 1:8 and/or up to 2:1. In some particularly preferred compositions, said weight ratio is from 1:2 and/or up to 3:2. By employing both types of triggered capsules, the composition is able to respond to both sweat events and normal movements of the body relative to other parts of the body and/or to clothing.

The weight of an encapsulated fragrance herein is the weight of the capsule, namely the combined weight of the encapsulated fragrance and the encapsulating material.

Shear sensitive capsules advantageously comprise a shell made from a water-insoluble gelatin coacervate or aminoplast encapsulating material. It is often convenient to employ one variety of shear-sensitive capsule, though a mixture of the two variations of shear-sensitive capsules can be employed. The shear sensitive capsules, particularly when made from water-insoluble gelatin coacervates, preferably have:

i). a volume average particle diameter in the range of 25 to 70 µm,
ii). a shell having a measured thickness in the range of from 0.25 to 9 µm and a Hysitron hardness in the range of from 1.5 MPa to 50 MPa, and
iii). a ratio of the shell thickness to the average particle diameter in the range of from 1:5 to 1:120 and preferably from 1:5 to 1:60.

In other desirable embodiments, in which the capsule comprises an aminoplast shell, the capsules preferably have:

i). a weight average particle diameter in the range of 25 to 60 µm,
ii). a shell having an average measured thickness in the range of from 2.5 to 8 µm and a Hysitron hardness in the range of from 1.5 MPa to 50 MPa and
iii). a ratio of the shell thickness to the average particle diameter in the range of from 1:3 to 1:20.

If desired, the composition can comprise both cross-linked gelatin coacervate capsules and aminoplast capsules.

The presence of cross-linked gelatin coacervate capsules is particularly preferred.

One encapsulation process suitable for forming shear sensitive capsules is often called complex coacervation, which has been described, for example, in U.S. Pat. No. 6,045,835. In such a process, an aqueous solution of a cationic polymer, commonly gelatin or a closely related cationic polymer, is formed at an elevated temperature that is high enough to dissolve the gelatin, commonly at least 40° and in many instances it is unnecessary to exceed 70° C. A range of 40 to 60° C. is very convenient. The solution is typically in the range of from 1 to 10% w/w and particularly from 2 to 5% w/w. Either before or after dissolution of the gelatin, an oil-in-water emulsion is formed by the introduction of a perfume oil, optionally together with a diluent oil if desired.

A polyanion or like negatively charged polymer is introduced and the composition diluted until a pH is attained of below the isoelectric point of the system, such as below pH 5, and particularly from pH 3.5 to pH 4.5, whereupon a complex coacervate forms around the dispersed perfume oil droplets. The polyanion commonly comprises gum arabic or a charged carboxymethyl cellulose derivative, such an alkali metal salt, of which sodium is the most commonly mentioned example.

The resultant shell is subsequently cross linked, with a short chain aliphatic di-aldehyde, for example a $C_4$ to $C_6$ dialdehyde, including in particular glutaraldehyde. The cross linking step is commonly conducted at a temperature of below ambient such as from 5 to 15° C., and particularly in the region of 10° C. Representative weights and proportions of the reactants and of suitable operating conditions are shown in Examples 1, 2 or 3 of the aforementioned U.S. Pat. No. 6,045,835. The skilled man by suitable selection of the parameters within the general process outlined therein is well capable of producing capsules having a volume average particle size in the range of from 30 to 100 µm, particularly up to 75 µm and especially 40 to 60 µm.

A second encapsulation method that is likewise suitable for forming encapsulated perfumes in which the shell comprises cross-linked coacervated gelatin comprises variations of the above process, as contemplated in WO2006/056096. In such variations, microcapsules comprising a blank hydrogel shell are first formed in a dry state and brought into contact with an aqueous or aqueous/alcoholic mixture of a fragrance compound, commonly diluted with a diluent oil. The fragrance compound is transported through the hydrogel shell by aqueous diffusion and is retained inside. The resultant fragrance-containing microcapsules are then dried to a powder, which for practical purposes is anhydrous. The ratio of fragrance oil to diluent oil is often selected in the range of from 1:2 to 1:1, and particularly 3:4 to 1:1.

The encapsulating material for shear-sensitive capsules in other desirable embodiments herein is desirably selected from aminoplast polymers, by which is meant resins obtained by polymerisation of an amine with an aliphatic aldehyde. The amine advantageously has a molecular weight of up to 150 and often at least 50. The aldehyde advantageously has a molecular weight of about 60, such as about 30 or 45.

The aminoplast-shelled microcapsules employable in the instant invention can be made in accordance with the general process described in U.S. Pat. No. 3,516,941, in which a disclosure in regard to urea is representative of the amine reactant generally, including melamine in particular. In such a process, in a first step, a low molecular weight amine-aldehyde precondensate is formed, advantageously urea or melamine with formaldehyde, suitably in an equivalent mole ratio of amine:aldehyde of 1:1.2 to 2.6 and preferably about 1:2. Preferably the reaction is alkaline catalysed and conducted in an aqueous medium at a pH in the range of from 7.5 to 11.0, at an elevated temperature below 100° C. and particularly from 50 to 90° C. The reaction is allowed to continue until the precondensate has formed to a desired extent, commonly selected in the range of from 15 minutes up to 3 hours, preferably correlating reaction time inversely with reaction temperature. The resultant precondensate is a water-soluble material that is dissolved in water at a concentration of from 3 to 30% by weight, preferably from 10 to 25% by weight.

The fragrance oil, together with any diluent oil if present, is introduced into the aqueous solution of the precondensate and subjected to intense mixing to form droplets that are distributed throughout the aqueous phase, the mixing intensity being controlled in a conventional manner so as to control the average diameter of the droplets. This stage of the process is conveniently conducted at a temperature of from 10 to 50° C., such as at ambient. It is desirable for the fragrance oil droplets to have an average diameter of from 25 to 55 µm, particularly at least 30 µm and in some especially desirable instances at least 35 µm. The dispersed droplets in some particularly suitable embodiments have a diameter of up to 45 µm.

The dispersion of the fragrance oil droplets in the precondensate solution is acidified by addition of acid to attain a solution pH in the region of from pH 1 to pH 5, in order to promote acid catalysis of the pre-condensate, with continued intense mixing of the solution. Particularly, the solution is acidified to below pH 3.5 or pH 3, and in many instances, the solution pH is not lower than pH 1.5. This stage of the process is often conducted at a temperature in the range of from about 20° C. to 90° C. and for a period of at least 1 hour. It is convenient and desirable to conduct this stage initially at a lower temperature of below 40° C., eg ambient, for a period of for example 20 to 60 minutes and thereafter to increase the temperature of the reaction mixture to within the range of from 60 to 90° C. for the remainder of the reaction period. The total reaction period is often not greater than 3 hours and in many instances is from 1.5 to 2.5 hours, and particularly including reaction at a temperature of at least 60° C. for from 45 to 90 minutes. In the event that the temperature were to be maintained below 60° C. throughout, the total reaction time is often up to 6 hours.

As a variation to acidification alone, the acid catalysis can be conducted in the additional presence of a mineral acid/alkali metal salt, such as sodium chloride, at a concentration of 2-20% by weight in the precondensate solution, and preferably at a pH in the range of from pH 4 to pH 5.

At the end of the acid catalysis, the capsules comprise a hard aminoplast shell surrounding a fragrance oil-containing core, forming an aqueous slurry. The aqueous phase is separated from the capsules, for example by filtration or centrifugation, and the capsules dried, for example until they have a residual moisture content of below 5% by weight and especially to below 3% by weight. Drying can be carried out by conventional means for sub 100 µm particles, such as by tray drying, commonly at a temperature of below 150° C. and often below 125° C., in order to avoid volatilising the fragrance oil or a significant fraction of it. Alternatively, the drying can be conducted under vacuum.

If desired, the manufacture process can be modified in accordance with the description in EP1797947, namely by the incorporation of a formaldehyde scavenger to, for example, the slurry containing the aminoplast capsules. The scavenger can be a beta dicarbonyl compound such as 1,3-cyclohexanedione, or manganese dioxide.

By control of the manufacturing process conditions, the resultant dry capsules having the characteristics specified in the ranges or preferred ranges for particles size and mean diameter described herein can be obtained.

It is desirable for the shell material of the encapsulates to constitute from at least 10% by weight of the capsules, commonly up to 80% by weight and for an aminoplast shell, is advantageously at least 30% by weight. A gelatin coacervate shell constitutes particularly from 10 to 40% by weight and especially from 12 to 25% by weight of the capsules, and an aminoplast shell often up to 80% and particularly from 35 to 60% by weight of the capsules. By varying the proportions of shell and core, the physical strength of the shell can be varied (for capsules of the same weight average particle size). Accordingly, capsules having the desired combination of characteristics can be selected. The balance of the weight of the capsules is provided by the contents of the core, which comprises the fragrance oil, optionally together with a diluent oil.

The average core volume of the capsules is desirably at least 25% and advantageously at least 30%. In many embodiments, the average core volume is up to 85% of the capsules, although for capsule with aminoplast shells, it is preferable for the core volume not to exceed. 60% and especially not to exceed 50%.

Advantageously, the fragrance oil is present in the core in a weight proportion of at least 20% of the capsules and especially at least 30% of the capsules. In many desirable embodiments, the weight proportion of fragrance oil in the capsules is up to 55% and particularly up to 50%. In other and preferred embodiments together in a gelatin coacervate shell, the fragrance oil constitutes greater than 55% and particularly from 70 to 85% by weight of the capsules. The balance of the core volume is provided by a diluent oil. Commonly any diluent oil provides not more than 75%, such as from 40 to 60% of the combined weight of fragrance plus diluent oil. In other embodiments the diluent oil provides not more than 25% of said combined weight. The diluent oil can comprise any oil that is employed as a carrier oil in fragrance compositions.

In certain much preferred embodiments employing a gelatin coacervate shell, the fragrance oil constitutes from 35 to 50% by weight of the capsules, and is complemented by 35 to 50% by weight of diluent oil. If desired, the composition contains some of the capsules that contain diluent oil and others that do not, the weight ratio of the two sets of capsules being selected in the range of from 25:1 to 1:25.

It is preferred for the volume average particle diameter (size) of the capsules to be at least 33 and particularly 40 μm and in many desirable embodiments is up to 60 μm in diameter. Herein, unless otherwise indicated, the volume average particle diameter of the capsules (D[4,3]) is that obtainable using a Malvern Mastersizer, the capsules being dispersed in cyclopentasiloxane (DC245) using a dispersion module mixer speed of 2100 rpm. Calculations are made using the General Purpose model, assuming a spherical particle shape and at Normal calculation sensitivity. The shell thickness can be measured by solidifying a dispersion of the capsules in a translucent oil, cutting a thin slice of the solid mass and using a scanning electron microscope to obtain an image of cut-through individual capsules, thereby revealing the inner and outer outline of its annular shell and hence its thickness. The shell thickness of the shear-sensitive microcapsules tends to increase as the particle size increases. The shell thickness accordingly, often ranges mainly within the thickness range of from 0.25 to 9 μm, and for capsules with aminoplast shells, the shell thickness is preferably at least 1 μm.

For many desirable capsules having shells made from coacervated gelatin, at least 90% by volume of the capsules have shells of up to 2.5 μm thickness. Desirably, at least 95% by volume of the capsules have a shell thickness of at least 0.25 μm. The average shell thickness of such gelatin coacervate microcapsules very desirably employed herein is up to 1.5 μm. The same or other suitable gelatin coacervate capsules have an average shell thickness of at least 0.4 μm. For capsules of diameter up to 40 μm, the shell thickness is often below 0.75 μm, such as from 0.25 to <0.75 μm whereas for particle of at least 40 μm the shell thickness is often from 0.6 to 2.5 μm.

The gelatin coacevate capsules for incorporation in the anhydrous antiperspirant compositions are commonly selected having a ratio of volume average diameter:average shell thickness in the range of from 10:1 to 100:1 and in many desirable such capsules in the range of from 30:1 or 40:1 to 80:1.

For capsules made with an aminoplast shell, those having a diameter up to 40 μm, the shell thickness is often below 6 μm, such as from 1 to 5 μm whereas for capsules of at least 40 μm the shell thickness is often from 4 or 5 to 10 μm. The average shell thickness of aminoplast-shelled capsules is often in the range of from 4 to 8 μm, particularly where the average capsule diameter is from 45 to 60 μm and in many desirable embodiments, the average shell thickness is at least 5 μm, such as in the region of 5.5 to 7 μm.

The hardness of the shear-sensitive capsules, as measured in a Hysitron Tribo-indenter, is an important characteristic that enables them to be incorporated effectively, for example in anhydrous formulations, retaining the capability of being sheared by frictional contact between skin and skin or clothing. The hardness is desirably in the range of from 0.5 to 50 MPa and especially from 2.5 or 5 up to 25 MPa, and in many embodiments is up to 10 MPa. In certain preferred embodiments, the hardness is in the range of from 3.5 to 5.5 MPa for gelatin coacervate capsules and from 2.5 to 4 MPa for aminoplast capsules.

A further parameter of interest in relation to the capsules used in the instant invention, and particularly their capability to be sheared by friction in the compositions and process of the instant invention, is their "Apparent Reduced Elastic Modulus (Er). Desirably, Er falls within the range of from 18 to 35 MPa, and in many convenient embodiments, in the range of from 22 to 30 MPa for gelatin coacervate capsule or 20 to 25 MPa for aminoplast capsules.

The hardness (Hysitron Hardness) and Apparent Reduced Elastic Modulus herein have values measured by the following method:—

A drop of a dispersion of the capsules in demineralised water is placed onto a piece of silicon wafer and allowed to dry leaving behind discrete micro capsules for mechanical analysis. The dried wafer is fitted into the Hysitron Tribo-indenter, and spatially mapped using the optical system of the instrument to identify a perimeter around the sample.

The head of the Tribo-indenter is fitted with a Berkovich tip, a three sided pyramid, which compresses individual capsules. A single capsule is positioned directly under the Indenter tip. The instrument is programmed to perform an indent by compressing the sample with an initial contact force of 75 μN, for 10 seconds, followed by a position hold stage for 1 second and a decompression stage for 10 seconds. The instrument achieves a very small load (typically around 15-30 μN). The Hysitron Hardness (H in MPa) and reduced Elastic Modulus (Er in MPa) are calculated from the relaxation stage of the force deflection data using the following equations.

$$H = \frac{W}{A}$$

W=Compressive force
A=Contact Area ($A \approx 24.56 h_c^2$)

$$Er = \frac{\sqrt{\pi}}{2\gamma} \frac{S}{\sqrt{A}}$$

S=Contact Stiffness ($dW/dh_t$)
$h_t$=Total Penetration Depth
$\gamma$=1.034

$$h_c = h_t - \kappa \frac{W}{S}$$

K=3/4
$h_c$=Contact Depth

Results are averages of a minimum of 20 measurements made on capsules with a particle size of D[4,3]+/−20%.

By control of the manufacturing process conditions, the resultant dry capsules having the characteristics specified in the ranges or preferred ranges for particles size and mean diameter described herein can be obtained.

The capsules often contain a small residual water content. It is desirable, for example, as measured by the conventional Karl Fischer method, to select capsules having a residual water content of below 5% by weight and particularly below 4% by weight, such as from 0.5 to 3.5% and particularly from 0.6 to 3% w/w (based on the fragrance-containing capsule). Based on the weight of the shell, said water content of the shear-sensitive capsules employed herein often falls in the range of from 1% to 20% w/w. By limiting the proportion of water in the capsule, and particularly in the shell, it is possible to avoid at least partly, and preferably substantially, the formation of grit within the anhydrous formulation, and thereby avoid the negative sensation of grit on underarm skin. Grit occurs typically when particles aggregate to form agglomerates that are not readily fractured into their constituent particles. Accordingly, in regard to aerosol or spray compositions, the avoidance of grit formation has a second benefit of reducing the likelihood of blockage of the spray nozzle.

In certain embodiments of the present invention, moisture-sensitive fragrance capsules are desirable. In such capsules, the capsule often comprises a matrix, in at least some instances resembling a sponge, possibly having an outer shell, and often comprising a plurality of voids within an individual capsule each of which can contain the fragrance oil. A wide variety of materials may serve as the encapsulation matrix. These materials may include synthetic and natural polymeric substances. Among the synthetic polymeric substances may be included polyethylene waxes, polyvinyl acetate, polyvinyl pyrrolidine, polyamides, polyesters, and homo- and co-polymers formed from monomers selected from the group consisting of acrylic, methacrylic, maleic, fumaric, itaconic acids and their esters and salts. Among suitable natural substances may be included polysaccharides, gelatin itself (not coacervated), gum acacia and gum arabic, carboxymethyl cellulose, hydroxyalkyl cellulose, and alkyl cellulose.

Most preferred are the polysaccharides, especially the modified starches comprising pendant alkyl esters such as up to C6, obtained conveniently by reaction of the substrate starch with an anhydride, and dextrins of low viscosity which include maltodextrins.

A particularly preferred example of the modified starches is Purity Gum BE which is a cornstarch which has been treated with succinic anhydride. An alternative encapsulating material is a maltodextrin known as Encapsul 855. Both of which aforementioned materials are available from the National Starch and Chemical Company.

The encapsulating matrix may form anywhere from about 10 to about 90%, preferably about 30 to about 75%, optimally between about 40 and 65% by weight of the capsule. The fragrance will be incorporated within the capsule at levels from about 10% to about 90%, preferably from about 30 to about 75% by weight of the capsule.

Average particle size of the capsule normally will range from about 1 to about 150 μm, preferably between from about 5 and 50 μm.

A variety of techniques may be used to form fragrance capsules. For instance, moisture-sensitive capsules can be formed by preparing an emulsion of water, the encapsulating material and the fragrance oil, together with any other oily materials dissolved or dispersed therein which are required to be included in the capsules. The emulsion is then spray-dried according to conventional technology to form the capsule.

By way of example, the moisture sensitive capsules can be prepared by forming an emulsion comprising from 20 to 40% preferably from 23 to 36% by weight of the encapsulating material and from 5 to 30 percent, preferably from 7 to 29 percent by weight of the fragrance oil, together with from 40 to 70 percent, preferably from 43 to 65 percent by weight water, by subjecting the composition to high shear mixing until the oil is distributed as droplets and thereafter spray-drying the emulsion. The oil is trapped within the resultant matrix.

Moisture-sensitive capsules so prepared often comprise approximately from 10 to 60 percent by weight of fragrance oil encapsuled by from 40 to 90 percent by weight of the encapsulating material. If desired, the capsules can further comprise a diluent oil, for example in a weight ratio to the fragrance oil of up to 1:1.

The weight proportion of encapsulated fragrances incorporated in the invention compositions herein is at the discretion of the product formulator. Commonly such compositions contain at least 0.1% by weight of encapsulated fragrances, based on the total weight of the composition (the total weight of the composition herein excluding any propellant, unless specified expressly to the contrary), often at least 0.3% by weight and in many desirable compositions, at least 0.5% by weight. Commonly, the compositions, the weight of encapsulated fragrance therein is up to 6% of the total composition weight, although a higher proportion such as up to 10% by weight can be contemplated. In many preferred compositions, the proportion of encapsulated fragrance is up to 4% of the total composition weight. The encapsulated fragrance can include moisture-sensitive capsules or not, such as in a weight ratio of moisture-sensitive to shear sensitive, water-insoluble of from 3:1 to 1:20, such as from 3:2 to 1:5.

In a number of preferred embodiments, the weight ratio of non-encapsulated fragrance to the fragrance present in the capsules (i.e. excluding the weight of the encapsulating material) falls within the range of from 5:1 to 1:5 and especially is up to 3:1, such as at least 1:1. If by way of example, the fragrance oil is present in the capsule at a concentration of 40% by weight together with 40% by weight of diluent oil, then such a ratio of 2:1 corresponds to a ratio of non-encapsulated fragrance to encapsulated fragrance of 4:5.

In anhydrous compositions, it is often desirable to employ a mixture of moisture and shear-sensitive encapsulated fragrances, though one alone can be employed. However, in aqueous compositions, i.e. compositions in which an aqueous phase is present, it is preferable to employ shear sensitive capsules as the encapsulated fragrance, or if it is desired to incorporate some moisture sensitive capsule, the weight ratio of the shear sensitive to the moisture sensitive capsule is at least 10:1.

The invention compositions herein contain both encapsulated fragrance and non-encapsulated fragrance. The combined weight of encapsulated and non-encapsulated fragrance is often at least 0.5% of the total composition weight and in many suitable compositions is up to 8% by weight thereof, and in many desirable embodiments is from 1 to 5% by weight of the composition. The weight of non-encapsulated fragrance is commonly at least 0.1% by weight of the total composition weight, often at least 0.2% and particularly at least 0.4%. In many desirable embodiments, the compositions contain up to 2% non-encapsulated fragrance based on the total composition weight (propellant-free) The weight ratio of the encapsulated fragrance to non-encapsulated fragrance is at the discretion of the formulator, but in practice is often at least 1:10, in many compositions at least 1:5 and in some preferred compositions at least 1:3. Said weight ratio is commonly up to 10:1, often up to 5:1 and in at least some desirable compositions is up to 3:1.

Subject to the aforementioned constraints, the respective fragrances can comprise any perfume component or preferably a mixture of components. Each fragrance commonly comprises at least 6 components, particularly at least 12 components and often at least 20 components. Such components can be extracts obtained from living or dead organisms, such as plants, including flowers, seeds, bark, and/or leaves, or can be synthetic, possibly mimicking natural extracts and mixtures can comprise mixtures of purely natural extracts, purely synthetic components or mixtures of both.

The boiling point of many fragrance components are disclosed in published compilations of perfume oils, such as in "Perfume and Flavor Chemicals" (Aroma Chemicals) by Stephan Arctander (1969). For some perfume oils, boiling point data is available from the supplier. For others, the boiling point can be measured by the skilled chemist. The components of a mixture can be separated for measurement of their boiling point, if necessary, by conventional analytic tools such as gas chromatography. For some oils, a boiling point measurement cannot be made at 1 bar pressure, for example if the component decomposes prematurely, and for such an oil, its boiling point is deemed to be that calculated on the basis of its chemical structure using the ACD/labs Inc programme for calculating boiling points on the Royal Society of Chemistry (UK) website www.chemspider.com. If any revisions to the programme should alter the calculated boiling point of a component, then its boiling point is deemed to be the altered boiling point rather than the superceded boiling point.

In addition to the boiling point of the fragrance components, the formulator of the various fragrances commonly takes into account the hydrophobicity of the fragrance, as shown by its ClogP (log to base 10 of the octanol/water partition coefficient). The perfume component oils herein commonly have a ClogP value of at least 0.1 and often at least 0.5.

Representative fragrance oils having a boiling point of below 250° C. at 1 bar pressure include the following materials:— anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, c is 1,3-oxathiane-2-methyl-4-propyl, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, and cis-3-hexenyl acetate.

Representative fragrance oils having a boiling point at 1 bar pressure of at least 250° C. include:— ethyl methyl phenyl glycidate, ethyl vanillin, heliotropin, indol, methyl anthranilate, vanillin, amyl salicylate, coumarin, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

The fragrances employed herein, either into the capsules or not encapsulated can comprise a pre-formed blend, either extracted from natural products, or possibly created synthetically. Representatives of such pre-formed blends include oils from:—

Bergamot, cedar atlas, cedar wood, clove, geranium, guaiac wood, jasmine, lavender, lemongrass, lily of the valley, lime, neroli, musk, orange blossom, patchouli, peach blossom, petitgrain or petotgrain, pimento, rose, rosemary, and thyme.

The liquid carrier is typically a carrier oil. It can comprise one or more oils, by which is meant liquids that are water-immiscible. Such oils are characterised by being liquid at 20° C. (at 1 atmosphere pressure) and are often selected from silicone oils, hydrocarbon oils, ester oils, ether oils and alcohol oils or a mixture of two or more oils selected from such classes of oils. It is highly desirable that the oil has a boiling point of above 100° C. and preferably above 150° C.

One class of oils that is highly favoured comprises volatile silicone oils, which often contribute from 20% to 95% by weight of a blend of oils, particularly at least 30% and in many convenient blends at least 40% by weight. It is advantageous in the instant invention to employ a blend in which the weight proportion of the volatile silicone oils is up to 80% by weight, and particularly up to 70% by weight.

Herein, a volatile silicone oil is a liquid polyorgano-siloxane having a measurable vapour pressure at 25° C. of at least 1 Pa, and typically in a range of from 1 or 10 Pa to 2 kPa. Volatile polyorganosiloxanes can be linear or cyclic or mixtures thereof. Preferred cyclic siloxanes, otherwise often referred to as cyclomethicones, include polydimethylsiloxanes and particularly those containing from 3 to 9 silicon atoms, preferably at least 4 and especially at least 5 silicon atoms. Preferred cyclomethicones contain not more than 7 silicon atoms and very preferably up to 6 silicon atoms.

Highly desirably, the compositions according to the present invention comprise either an ether oil or an ester oil or both, preferably in a proportion of greater than 10% w/w of the composition, and particularly greater than 20% w/w. Although together they could constitute up to 100% w/w of the carrier oil, it is desirable that together they contribute no greater than 60% w/w and in many compositions, they total up to 50% w/w of the total carrier oil.

The ester oils can be aliphatic or aromatic. Suitable aliphatic ester oils comprise at least one residue containing from 10 to 26 carbon atoms and a second residue of at least 3 carbon atoms up to 26 carbon atoms. The esters may be mono or diesters, and in the latter be derived from a $C_3$ to $C_8$ diol or di carboxylic acid. Examples of such oils include isopropyl myristate, isopropyl palmitate, myristyl myristate.

It is especially desirable to employ an aromatic ester, including especially benzoate esters. Particularly preferably, the aromatic ester comprises $C_{12-15}$ alkyl benzoate.

The ether oil, when present, preferably comprises a short chain alkyl ether of a polypropylene glygol (PPG), the alkyl group comprising from C2 to C6, and especially C4 and the PPG moiety comprising from 10 to 20 and particularly 14 to 18 propylene glycol units. An especially preferred ether oil is PPG14-butyl ether.

The ester and ether oils can be present in the composition in a weight ratio to each other of from 1:0 to 0:1 and in some embodiments from 10:1 to 1:10.

The carrier oil can further comprise one or more other water-immiscible oils that have a melting point of below 20° C. and a boiling point of above 100° C. and preferably above 150° C., including hydrocarbon oils, including preferably non-volatile hydrocarbon oils, non-volatile silicone oils and aliphatic monohydric alcohols.

The weight of fragrance materials is not included herein in calculating the weight of the oil carrier, irrespective of whether the fragrance is encapsulated or "free".

Although it is particularly suitable to employ anhydrous compositions herein, which is to say compositions that do not contain a discernible aqueous phase, any water present being associated with some other ingredient, in some embodiments of the present invention, the antiperspirant or deodorant compositions can additionally comprise an aqueous phase, and commonly together with an oil phase, the composition is in the form of an emulsion. In such compositions, the aqueous phase commonly constitutes from 10% and particularly from 30% by weight of the total composition, often up to 97% by weight. The balance of the composition comprises the oil phase, including any suspended material and the emulsifier or emulsifiers. Emulsions according to the present invention particularly suitably comprise shear-sensitive encapsulated fragrance.

The composition preferably contains an antiperspirant active. Antiperspirant actives are preferably incorporated in an amount of from 0.5-50%, particularly from 5 to 30% and especially from 10% to 26% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_x Q_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al).

Zirconium actives can usually be represented by the empirical general formula: $ZrO(OH)_{2n-nz} B_z \cdot wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

Antiperspirant complexes based on the above-mentioned astringent aluminium and/or zirconium salts can be employed. The complex often employs a compound with a carboxylate group, and advantageously this is an amino acid.

Examples of suitable amino acids include dl-tryptophan, dl-β-phenylalanine, dl-valine, dl-methionine and β-alanine, and preferably glycine.

It is highly desirable to employ complexes of a combination of aluminium halohydrates and zirconium chlorohydrates together with amino acids such as glycine, which are disclosed in U.S. Pat. No. 3,792,068 (Luedders et al).

The proportion of solid antiperspirant salt in a suspension (anhydrous) composition normally includes the weight of any water of hydration and any complexing agent that may also be present in the solid active.

For incorporation of compositions according to the present invention, desirably at least 90%, preferably at least 95% and especially at least 99% by weight of the particles have a diameter in the range of from 0.1 μm up to 100 μm, and usually have an average particle diameter of at least 1 μm and especially below 20 μm. In some highly desirable contact compositions the particles by weight have a weight average particle size of at least 2 μm and particularly below 10 μm, such as in the range of from 3 to 8 μm.

Compositions according to the invention may be emulsions. In such compositions, the antiperspirant active is commonly dissolved in the aqueous phase, commonly at a weight concentration in that phase of between 10 and 55%. In many suitable emulsions, the concentration of antiperspirant active is chosen in relation to the weight of oils (including any non-encapsulated fragrance oils), decreasing progressively from a ratio of about 3:1 to 5:1 when the proportion of oils is below 10% to a ratio in the range of 3:2 to 2:3 when the oils content is at least 50% of the total weight of the composition (excluding any propellant).

The invention compositions may include one or more thickeners or gellants (sometimes called structuring or solidifying agents) to increase the viscosity of or solidify the liquid carrier in which the particulate materials are suspended as is appropriate for application from respectively soft solid (anhydrous cream) dispensers or stick dispensers.

Compositions according to the invention may be stick compositions. Such compositions desirably have a hardness as measured in a conventional penetration test (Seta) of less than 30 mm, preferably less than 20 mm and particularly desirably less than 15 mm. Many have a penetration of from 7 to 13 or 7.5 to 10 or 12.5 mm. The conventional penetration test employed herein, utilises a lab plant penetrometer equipped with a Seta wax needle (weight 2.5 grams) which has a cone angle at the point of the needle specified to be 9° 10'+/−15'. A sample of the composition with a flat upper surface is used. The needle is lowered onto the surface of the composition and then a penetration hardness measurement is conducted by allowing the needle with its holder to drop under the combined weight of needle and holder of 50 grams for a period of five seconds after which the depth of penetration is noted. Desirably the test is carried out at six points on each sample and the results are averaged.

The gellants for forming stick compositions herein are usually selected from one or more of two classes: non-polymeric fibre-forming gellants and waxes, optionally supplemented by incorporation of a particulate silica and/or an oil-soluble polymeric thickener.

Waxes, when employed, are often selected from hydrocarbons, linear fatty alcohols, silicone polymers, esters of fatty acids or mixtures containing such compounds along with a minority (less than 50% w/w and often less than 20% w/w) of other compounds.

Non-polymeric fibre-forming gellants, when employed, are typically dissolved in a water-immiscible blend of oils at elevated temperature and on cooling precipitate out to form a network of very thin strands that are typically no more than a few molecules wide. One particularly effective category of such thickeners comprises N-acyl aminoacid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions according to the present invention, if desired, with 12-hydroxystearic acid.

A gellant is often employed in a stick or soft solid composition at a concentration of from 1.5 to 30%, depending on the nature of the gellant or gellants, the constitution of the oil blend and the extent of hardness desired.

The anhydrous compositions can contain one or more optional ingredients, such as one or more of those selected from those identified below.

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts. Such adjuncts can include skin feel improvers, such as talc or finely divided (i.e. high molecular weight) polyethylene, i.e. not a wax, for example Accumist™, in an amount of 1 up to about 10%; a moisturiser, such as glycerol or polyethylene glycol (mol wt 200 to 600), for example in an amount of up to about 5%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A further optional ingredient comprises a preservative, such as ethyl or methyl parabens or BHT (butyl hydroxy toluene) such as in an amount of from 0.01 to 0.1% w/w.

The invention composition and particularly compositions intended to be delivered from a roll-on dispenser or a pump spray, conveniently comprise emulsions. In such emulsions the total oil content is often less than 10% by weight of the total composition, for example comprising between 0.5 and 2% by weight of fragrance oils (non-encapsulated) and from 1 to 6% by weight of other oils, selected for example from the carrier oils described hereinbefore. It is particularly suitable to employ from 1 to 5% by weight of a triglyceride oil, such as sunflower seed oil.

Emulsions commonly employ a non-ionic surfactant acting as an emulsifier or mixture of emulsifiers providing an HLB value in the region of 6 to 10. An especially desirable range of emulsifiers comprises a hydrophilic moiety provided by a polyalkylene oxide (polyglycol), particularly polyethylene oxide, such as containing 4 to 6 EO units or a mixture of 2-4 plus 10 to 30 EO units and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol.

Preferably the hydrophobic aliphatic substituent contains at least 12 carbons, and is derivable from lauryl, palmityl, cetyl, stearyl, olearyl and behenyl alcohol, and especially cetyl, stearyl or a mixture of cetyl and stearyl alcohols or from the corresponding carboxylic acids. Particularly conveniently, the combination of emulsifiers comprises steareth-2 and a selection from steareth-15 to steareth-30.

The invention compositions desirably are substantially or totally free from water-soluble short chain monohydric alcohols (commonly recognised as up to $C_6$) and especially ethanol. Substantially in this context indicates a proportion of less than 5% and preferably less than 1% by weight of the respective full or base composition.

Herein unless the context demands otherwise, all weights, percentages, and other numbers can be qualified by the term "about".

Compositions according to the invention may be aerosol compositions. Such compositions herein comprise a base composition, namely a full composition except for a propellant mixed with a propellant. The base composition commonly comprises the antiperspirant and/or deodorant active, the liquid carrier and often a suspending aid.

Many suitable aerosol compositions are anhydrous. Such compositions typically have a proportion of carrier oils that is commonly from 50 to 95% by weight of the base composition, and the mixture commonly includes one or more volatile oils such as a volatile silicone oil and one or more non-volatile oils, often in a weight ratio of from 10:1 to 1:2 and particularly from 5:1 to 1:1. The concentration antiperspirant active in the base composition is often from 5% to 60% and especially 10% to 45% by weight.

During the manufacture of compositions according to the invention, it is especially desirable for the fragrance capsules to be incorporated into the composition with mixing at a rate and power input that does not damage the capsules.

One convenient process sequence for preparing a stick or soft composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the gellants. However, the fragrance oil, be it encapsulated or free, is commonly the last ingredient to be incorporated into the composition, after the antiperspirant active on account of its sensitivity often to elevated temperature. Commonly the resultant structurant solution is allowed to cool to a temperature that is intermediate between that at which the gellants dissolved and the temperature at which it would set, often reaching a temperature in the region of 60 to 90° C.

In some routes, the carrier oils can be mixed together prior to introduction of the gellants and the antiperspirant or deodorant active. In other preparative routes, it is desirable to dissolve all or a fraction of the gellants and especially for amido gellants in a first fraction of the composition, such as a branched aliphatic alcohol, e.g. isostearyl alcohol or octyldodecanol, optionally in conjunction with an alcohol having some water-miscibility and boiling point above the dissolution temperature of the amido gellant in the alcoholic fluid. This enables the remainder of the carrier fluids to avoid being heated to the temperature at which the structurants dissolve or melt. Such a process commonly involves mixing the fractions intensively in for example a "Sonolator"™. In the invention compositions, the fragrance capsules are most desirably introduced after any intensive mixing step. The proportion of the carrier fluids for dissolving the structurants is often from 25 to 50% by weight of the carrier fluids.

In other preparative routes the particulate material is introduced into preferably a second fraction of the carrier oils, for example silicone and/or ester and/or hydrocarbon oils and thereafter, and thereafter the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature.

EXAMPLES

The Examples and comparisons described hereinafter employed fragrances as characterised as below. The % s of components satisfying the boiling point ranges were obtained by first identifying the components of the fragrances, identifying their % in the fragrance and identifying their boiling point, either from published literature or by calculation employing the ACD/labs Inc programme for calculating boiling points on the Royal Society of Chemistry (UK) website: www.chemspider.com.

TABLE 1

| | | % of components satisfying boiling point (° C.) | | | | | |
|---|---|---|---|---|---|---|---|
| | | ≤250 C. | >250 C. | ≤220 C. | >220 C. | ≤270 C. | >270 C. |
| Non-encapsulated Fragrance | | | | | | | |
| code | High BP rich | | | | | | |
| M1 | Yes | 19 | 81 | 11 | 89 | 22 | 78 |
| M2 | Yes | 26 | 74 | 17 | 83 | 29 | 71 |
| M3 | Yes | 14 | 86 | 7 | 93 | 15 | 85 |
| M4 | No | 45 | 55 | 24 | 76 | 57 | 43 |
| Encapsulated Fragrance | | | | | | | |
| code | High BP lean | | | | | | |
| R1 | Yes | 36 | 64 | 28 | 72 | 40 | 60 |
| R2 | Yes | 45 | 55 | 32 | 68 | 58 | 42 |
| R3 | No | 15 | 85 | 6 | 94 | 17 | 83 |
| R4 | Yes | 60 | 40 | 16 | 84 | 72 | 28 |

Encapsulating Processes to Encapsulate Fragrances R1 to R4

Encapsulating process E2 was in accordance with U.S. Pat. No. 6,045,835, in which process an aqueous solution of a cationic polymer, commonly gelatin or a closely related cationic polymer, was formed at an elevated temperature that is high enough to dissolve the gelatin, commonly at least 40° and not exceeding 70° C. The solution was typically dilute, falling in the range of from 2 to 5% w/w. Either before or after dissolution of the gelatin, an oil-in-water emulsion was formed by the introduction of a perfume oil, optionally together with a diluent oil if present.

A polyanion or like negatively charged polymer was introduced and the composition diluted until a pH attained of below the isoelectric point of the system, from pH 3.5 to pH 4.5, whereupon a complex coacervate formed around the dispersed perfume oil droplets. The polyanion comprised an alkali metal salt of carboxymethyl cellulose.

The resultant shell was subsequently cross linked with glutaraldehyde at a temperature of from 5 to 15° C. Representative weights and proportions of the reactants and of suitable operating conditions are shown in Examples 1, 2 or 3 of the aforementioned U.S. Pat. No. 6,045,835.

Encapsulating process E1 employed a modification of the E2 process and was in accordance with the process described in WO2006/056096, employing the coacervate of gelatin with gum arabic. The cross linking agent was glutaraldehyde.

In such a modification, microcapsules comprising a blank hydrogel shell was first formed in a dry/damp state and brought into contact with an aqueous or aqueous/alcoholic mixture of a fragrance compound, commonly diluted with a diluent oil. The fragrance compound was transported through the hydrogel shell by aqueous diffusion and retained inside. The resultant fragrance-containing microcapsules were employed without drying, being a paste or liquid dispersion, or can be dried to a powder, which for practical purposes is anhydrous.

In both processes, the preparative conditions employed were controlled to obtain the specified shell wall and capsule hardness characteristics identified in Table 2 below.

TABLE 2

| Characteristic | E1 Capsules | E2 Capsules |
|---|---|---|
| Mean particle size D[4,3] | 48.4 µm | 50.7 µm |
| Shell thickness (19 to 38 µm) | 0.3-0.65 µm | |
| Shell thickness (25 to 35 µm) | | 0.25-0.6 µm |
| Shell thickness calculated at mean particle size | 1.0-1.6 µm | 1.4-2.2 µm |
| DR (11 to 18 µm) | 40:1-58:1 | 60:1-100:1 |
| DR (calculated shell thickness) | 30:1-48:1 | 23:1-36:1 |
| Hysitron hardness | 4.05 MPa | 4.88 MPa |
| Apparent Reduced Elastic Modulus | 24.1 MPa | 27.5 MPa |
| Wt % oils/fragrance in core | 85/40 | 80/80 |

Mean Particle Size: D[4,3] of the capsules after dispersion in volatile silicone (cyclopentadimethicone) was obtained using a Malvern Mastersizer 2000, the following parameters.
RI of Dispersant=1.397
RI of capsule E1=1.430
RI of capsule E2=1.530
Dispersion module mixer speed=2100 rpm.
Result calculation model=General purpose.
Calculation sensitivity=Normal.
Particle shape=Spherical Shell Thickness: Measured by SEM on encaps with a particle size specified. For non-spherical encaps, the thickness was measured at or close to the minimum capsule diameter.

Shell Thickness (Calculated): Calculation assumed that capsules were spherical, with a single core and the shell and core had the same density. DR is the ratio of average. particle diameter measured shell thickness.

In the Examples and Comparisons herein, antiperspirant compositions as described in Table 3 below was made by a conventional method for making respectively an anhydrous antiperspirant stick composition that is gelled by waxes or an anhydrous aerosol composition. In the stick compositions, the fragrance or mixture of fragrances was the last ingredient introduced into the composition, after it had cooled to a temperature in the region of 60 to 65° C. and shortly before it was introduced into the plastic barrels of conventional dispensers of such compositions. For aerosol compositions, the aerosol base was diluted conventionally in the aerosol canister with hydrocarbon (propane/butane/isobutane) propellant (CAP40™) in a weight ratio of 13:87.

TABLE 3

| Ingredient | Stick | Aerosol Base |
|---|---|---|
| | % by weight | |
| Cyclomethicone | balance | Balance |
| Ester oil | 15.0 | |
| Ether Oil | 9.5 | 23.1 |
| Dimethiconol in cyclomethicone | | 3.8 |

TABLE 3-continued

| Ingredient | Stick % by weight | Aerosol Base % by weight |
|---|---|---|
| Stearyl alcohol | 18.0 | |
| Castorwax | 3.5 | |
| Polyethylene wax | 1.0 | |
| Suspending Aid | | 3.8 |
| Swelling Aid | | 0.1 |
| AZAG | 24.00 | |
| AACH | | 38.5 |
| AP cogellant | | 3.8 |
| Preservative | 0.05 | |
| Fragrance/amount | As specified | As specified |

The effectiveness of the fragrances was tested by the following method:—

The effectiveness was determined in the following test in which 24-26 panelists self-applied approximately 0.3 g example stick product to either the left or right armpit and comparison product to the other, with overall left-right randomized balance or an approximately 2 second spray.

After application of the antiperspirant formulations, the users put on their normal clothing and the intensity of the odour was assessed at 2 hourly intervals on a scale of perception increasing from 0 to 10. The scores were averaged and that for the non-encapsulated sample deducted from that for the encapsulated sample. Three scores were measured, namely intensity of the fragrance itself, the intensity detected through the clothing and finally the intensity of any malodour and tabulated.

Examples 1 and 2 and Comparisons C1 and C2

These Examples and comparisons compared the effect of employing encapsulated fragrance R2 with encapsulated fragrance R3 in compositions that contained non-encapsulated fragrance M2 or M3. In Ex1/Comp 1, all four stick composition contained non-encapsulated fragrance M2 in an amount of 1.2% by weight. Two compositions contained additionally 0.7% by weight of E2 capsules providing 0.56% by weight of fragrance, Ex1 providing R2 and C1 providing R3. In Ex2/Comp 2, all four stick composition contained non-encapsulated fragrance M3 in an amount of 1.5% by weight. Two compositions contained additionally 0.7% by weight of E2 capsules providing 0.56% by weight of fragrance, Ex1 providing R2 and C1 providing R3. The intensity assessment scores are summarised in Tables 4 and 5 below.

TABLE 4

| | Intensity Score at assessment | | | | Gain in Intensity at assessment | | |
|---|---|---|---|---|---|---|---|
| Assess- | Ex 1 | | Comp 1 | | Ex 1 | Comp 1 | Ex 1 |
| ment time (Hrs) | M2 | M2 + R2 | M2 | M2 + R3 | M2 + R2 vs M2 | M2 + R3 vs M2 | minus C1 |
| 0 | 4.83 | 4.91 | 4.63 | 4.75 | 0.09 | 0.12 | −0.03 |
| 2 | 2.75 | 4.79 | 3.50 | 3.33 | 2.04 | −0.17 | 2.21 |
| 4 | 2.13 | 4.54 | 2.54 | 2.58 | 2.41 | 0.04 | 2.37 |
| 6 | 1.92 | 4.08 | 1.88 | 2.38 | 2.16 | 0.5 | 1.66 |
| 8 | 1.33 | 3.29 | 1.29 | 1.79 | 1.96 | 0.5 | 1.46 |
| 10 | 1.14 | 3.04 | 1.13 | 1.63 | 1.90 | 0.5 | 1.4 |
| 12 | 0.96 | 2.54 | 1.08 | 0.96 | 1.58 | −0.12 | 1.7 |
| 14 | 0.42 | 1.79 | 0.58 | 0.58 | 1.37 | 0.0 | 1.37 |

TABLE 5

| | Intensity Score at assessment | | | | Gain in Intensity at assessment | | |
|---|---|---|---|---|---|---|---|
| Assess- | Ex 2 | | Comp 2 | | Ex 2 | Comp 2 | Ex 2 |
| ment time (Hrs) | M3 | M3 + R2 | M3 | M3 + R3 | M3 + R2 vs M3 | M3 + R3 vs M3 | minus C2 |
| 0 | 3.94 | 4.85 | 4.15 | 4.73 | 1.31 | 0.59 | 0.62 |
| 2 | 2.96 | 4.58 | 2.69 | 2.69 | 1.62 | 0 | 1.62 |
| 4 | 2.54 | 4.23 | 2.35 | 2.07 | 1.69 | −0.28 | 1.97 |
| 6 | 2.15 | 3.69 | 1.92 | 1.69 | 1.54 | −0.23 | 1.77 |
| 8 | 1.77 | 3.31 | 1.73 | 1.77 | 1.54 | −0.04 | 1.58 |
| 10 | 1.35 | 2.92 | 1.42 | 1.42 | 1.57 | 0.0 | 1.57 |
| 12 | 1.04 | 2.57 | 1.15 | 1.23 | 1.54 | 0.12 | 1.66 |
| 14 | 0.92 | 1.85 | 0.73 | 0.77 | 0.93 | 0.04 | 0.97 |

Table 4 demonstrates that there is a significant gain in fragrance intensity from 2 hours to 14 hours for the composition containing the encapsulated fragrance compared with the one that did not, when the encapsulated fragrance was in accordance with the present invention, but the effect was either absent or much smaller when the encapsulated fragrance was not in accordance with the present invention. Consequently, the present invention provides a significant fragrance intensity on application and an intensity that is maintained at a high level for an extended period of time. Table 5 demonstrates the same beneficial outcome.

Examples 1 and 2 demonstrate that the combination of fragrances in accordance with the present invention provide the user with an significantly increased fragrance intensity over an extended period of time, the measurements being conducted over a period of 14 hours after application of the antiperspirant compositions. Accordingly the selected combination of non-encapsulated and encapsulated fragrances is particularly suitable for a leave on product which is commonly intended to remain in place on skin for a long period of time after application that is typically in either the morning or evening after washing, until it is washed off, often in the evening after a morning application, or in the morning after an evening application.

In comparisons C1 and C2, the encapsulated fragrance was not in accordance with the invention selection of fragrances and failed to provide a long lasting fragrance intensity to anything like the same extent as in Examples 1 and 2 employing otherwise exactly the same composition.

Example 3 and Comparisons C3 and C4

These Examples and comparisons compared the effect of employing encapsulated fragrance R1 with encapsulated fragrance R3 in compositions that contained non-encapsulated fragrance M1 or M4. In Ex3/Comp 3, all four composition contained non-encapsulated fragrance M1 in an amount of 0.6% by weight in the aerosol composition. Two of those compositions contained additionally 0.3% by weight of E2 capsules providing 0.24% by weight of fragrance, Ex3 providing R1 and C3 providing R3. In Comp 4, both compositions contained non-encapsulated fragrance M4 in an amount of 1.0% by weight and one contained additionally 0.3% by weight of E2 capsules providing 0.24% by weight of fragrance R1. The intensity assessment scores are summarised in Tables 6 and 7 below.

TABLE 6

| Assessment time (Hrs) | Intensity Score at assessment | | | | Gain in Intensity at assessment | | |
|---|---|---|---|---|---|---|---|
| | Ex 3 | | Comp 3 | | Ex 3 | Comp 3 | Ex 3 |
| | M1 | M1 + R1 | M1 | M1 + R3 | M1 + R1 vs M1 | M1 + R3 vs M1 | over C3 |
| 0 | 4.75 | 5.00 | 4.69 | 4.84 | 0.25 | 0.15 | 0.1 |
| 2 | 2.94 | 4.00 | 3.50 | 3.61 | 1.06 | 0.11 | 0.95 |
| 4 | 2.25 | 3.19 | 2.50 | 2.63 | 0.94 | 0.13 | 0.81 |
| 6 | 1.75 | 2.75 | 1.88 | 1.94 | 1.00 | 0.06 | 0.94 |
| 8 | 1.31 | 2.44 | 1.43 | 1.63 | 1.13 | 0.20 | 0.93 |
| 10 | 1.13 | 1.88 | 1.06 | 1.02 | 0.75 | −0.04 | 0.79 |
| 12 | 0.88 | 1.50 | 0.81 | 0.84 | 0.62 | 0.03 | 0.59 |

TABLE 7

| Assessment time (Hrs) | Intensity Score at assessment Comp 4 | | |
|---|---|---|---|
| | M4 | M4 + R1 | M4 + R1 vs M4 |
| 0 | 5.38 | 5.31 | −0.07 |
| 2 | 4.25 | 4.38 | 0.13 |
| 4 | 3.88 | 3.81 | −0.07 |
| 6 | 3.44 | 3.07 | −0.37 |
| 8 | 2.75 | 2.94 | 0.19 |
| 10 | 2.50 | 2.75 | 0.25 |
| 12 | 1.94 | 1.81 | −0.13 |

In Example 3, the combination of non-encapsulated and encapsulated fragrances meet the invention fragrance boiling point criteria, whereas in comparison C3, the encapsulated fragrance does not, so that the combination does not. Table 6 demonstrates that the invention combination of fragrances in Example 3 provides a significantly higher fragrance intensity over an extended period of time compared with the combination as shown in comparison C3 that does not.

Table 7 demonstrates the effect of employing a different combination of non-encapsulated and encapsulated fragrances not in accordance with the invention. In this combination, both of the fragrances M4 and R1 are comparatively rich in fragrance components having a boiling point of up to 250° C. The data in Table 7 shows that over an extended period of time there is little difference in effect arising from the presence of the encapsulated fragrance.

Examples 5 to 8 and Comparisons 5 to 8

Malodour Data

In these Examples and comparisons, invention and comparison compositions were compared at suppressing malodour by the following clinical method:—

Test and control product was applied daily to the underarm of panelists (0.3 g+/−0.03 g) and the panelist carried out normal daily activities until after 5 or 24 hours, the effectiveness of the fragrance was assessed by the trained assessor sniffing the exposed underarm. The malodour was assessed on a scale of from 0 to 5.

The assessments were made using a roll-on formulation described below in Table 8 and stick formulations in accordance with Table 2. The roll-on formulation was made in a convention way, containing 1% non-encapsulated fragrance M2 and 0.7% E2 encapsulated fragrance (providing 0.56% fragrance), being R2 in Example 5 and R3 in Comparison C5.

TABLE 8

| Roll-on Formulation | |
|---|---|
| Ingredient | % by weight |
| Water | Balance |
| ACH (50% w/w solution) | 30.0 |
| Triglyceride oil | 2.0 |
| Steareth-2 | 2.3 |
| Steareth-20 | 0.9 |
| Hydrophobic silica | 0.7 |
| Fragrance/amount | As specified |

TABLE 9

| | Ex 5 | C 5 |
|---|---|---|
| Non-encapsulated Fragrance | M2 | M2 |
| Encapsulate Fragrance | R2 | R3 |
| Encapsulate | E2 | E2 |
| *Delta Malodour Score (5 hrs) | 0.11 | 0.06 |
| *Delta Malodour Score (24 hrs) | 0.14 | −0.02 |

In the Examples and Comparisons herein, *Delta Malodour Score is the difference between the score for formulation with unencapsulated fragrance but no encapsulated fragrance and the score for otherwise identical formulation with containing both non-encapsulated and encapsulated fragrances.

Table 9 demonstrates that the antiperspirant composition containing the combination of fragrances in accordance with the present invention resulted in an improved, positive suppression of malodour in a clinical trial at both 5 and 24 hours. Indeed, the improvement increased as time passed. On the other hand when a combination not according to the invention was employed, the improvement detected after 5 hours was only half that from the invention combination and after 24 hours no improvement was detectable after 24 hours.

Stick Formulations

In Example 6 and Comparison C6, the compositions contained 1.2% non-encapsulated fragrance M2 plus 0.7% E2 encapsulates providing 0.56% fragrance, respectively R2 and R3.

In Ex 7 and Comp 7, the compositions contained 1.5% non-encapsulated fragrance M3 plus 0.7% E2 encapsulates providing 0.56% fragrance, respectively R2 and R3.

In Ex 8 and Comp 8, the compositions contained 1.5% non-encapsulated fragrance respectively M3 or M4 plus 1.5% E1 encapsulates providing 0.56% fragrance.

TABLE 10

| | Ex 6 | C 6 | Ex 7 | C 7 | Ex 8 | C 8 |
|---|---|---|---|---|---|---|
| Fragrances | M2/R2 | M2/R3 | M3/R2 | M3/R3 | M3/R2 | M4/R2 |
| Encapsulating Process | E2 | E2 | E2 | E2 | E1 | E1 |
| *Delta Malodour Score (5 hrs) | 0.12 | −0.03 | 0.36 | 0.01 | 0.26 | 0.07 |
| *Delta Malodour Score (24 hrs) | 0.10 | 0.00 | 0.14 | −0.14 | 0.10 | −0.06 |

Table 10 demonstrates that the compositions containing the combination of non-encapsulated fragrance and encapsulated fragrance according to the present invention provided a positive malodour suppression after both 5 hours whereas the two different types of composition not according to the present invention (as shown in C6/C7 and C8 respectively)

did not show such a positive odour suppression improvement, typically showing zero or impaired odour suppression after 24 hours.

Examples 9 and 10 and Comparisons C9 to C12

In-vitro Data-Fragrance Component Level

These Examples and Comparisons demonstrate how the fragrance compositions and their character change over time using in-vitro fragrance evaporation rate data.

The evaporation rate of the fragrance components in both the non-encapsulated and encapsulated fragrances (as a free oil) and summarized in Table 11 below as "low BP" (boiling points≤250° C.) and "high BP" (boiling points>250° C.) were measured as described below at the specified time intervals to show how they changed, and thus how the balance of the fragrances would change.

The measurement of evaporation rates (residual fragrance composition) was measured as follows:—

0.375 ml of the fragrance oil was weighed onto a grade 541 filter paper, which was placed into the bottom of a 60 ml glass jar (the diameter of the jar opening was 3.3 cm). The filter paper had been cut previous to size to cover the entire base of the jar. The bottle was then place in a fan assisted oven thermostated at 37° C. for the required period of time. The bottle was removed, capped and allowed to cool. 10 ml of ethanol was pipetted into the jar to dissolve the remaining fragrance, and then the solution analysed by GC/MS. The total amount of fragrance components in each of the two boiling point regions was then totalled. Duplicate samples were prepared and analysed for each time point.

The % by weight of each component fraction as a function of time for non-encapsulated fragrances M4 and M3 alone are shown separately for comparison.

In normal use, the encapsulated fragrance releases over many hours and the fragrance components begin to evaporate as they release. To represent this phenomenon, the encapsulated fragrance was assumed to release at a constant rate over a 14 hour period, and evaporate at the rate measured by the method above from the point of release. The resulting released fragrance composition profile generated by this method was then superimposed on top of that for the mother fragrance. The wt ratio of mother fragrance:encapsulated fragrance was 1:0.3 in all cases.

The composition profiles for the non-encapsulated+released encapsulated fragrance are summarized in Tables 11 and 12 below.

In the combination M4/R3, neither fragrance meets the invention composition selection criteria.

In the combinations M4/R2 and M4/R4, the encapsulated fragrance meets the second part of the invention combination selection criteria but the non-encapsulated fragrance does not meet the first part.

In the combination M3/R3, the non-encapsulated fragrance meets the first part the invention combination selection criteria but the encapsulated fragrance does not meet the second part.

In the combination M3/R2 and M3/R4, both fragrances meet their respective parts of the invention Combination selection criteria. As can be see with the invention combination the amount of non-evaporated components remain more constant with time. This is particularly true for the top notes which have greater intensity.

TABLE 11

| Time hrs | M4 alone Low BP | M4 alone High BP | Comp 9 M4/R3 Low BP | Comp 9 M4/R3 High BP | Comp 10 M4/R2 Low BP | Comp 10 M4/R2 High BP | Comp 11 M4/R4 Low BP | Comp 11 M4/R4 High BP |
|---|---|---|---|---|---|---|---|---|
| 0 | 100 | 100 | 100 | 100 | 100 | 100 | 100 | 100 |
| 1 | 89 | 99 | 90 | 103 | 93 | 101 | 92 | 101 |
| 2 | 79 | 99 | 81 | 107 | 85 | 103 | 86 | 103 |
| 4 | 63 | 98 | 66 | 114 | 72 | 107 | 75 | 105 |
| 6 | 57 | 97 | 54 | 120 | 62 | 111 | 66 | 108 |
| 8 | 40 | 96 | 44 | 127 | 53 | 114 | 60 | 111 |
| 10 | 32 | 95 | 37 | 134 | 46 | 118 | 54 | 113 |
| 12 | 26 | 94 | 30 | 140 | 40 | 122 | 51 | 115 |

TABLE 12

| Time hrs | M3 alone Low BP | M3 alone High BP | Comp 12 M3/R3 Low BP | Comp 12 M3/R3 High BP | Example 9 M3/R2 Low BP | Example 9 M3/R2 High BP | Example 10 M3/R4 Low BP | Example 10 M3/R4 High BP |
|---|---|---|---|---|---|---|---|---|
| 0 | 100 | 100 | 100 | 100 | 100 | 100 | 100 | 100 |
| 1 | 88 | 100 | 91 | 102 | 97 | 101 | 98 | 101 |
| 2 | 77 | 100 | 82 | 104 | 94 | 103 | 98 | 102 |
| 4 | 59 | 99 | 68 | 109 | 89 | 105 | 98 | 104 |
| 6 | 52 | 99 | 57 | 113 | 85 | 108 | 99 | 106 |
| 8 | 35 | 99 | 49 | 118 | 82 | 110 | 102 | 107 |
| 10 | 27 | 98 | 42 | 122 | 79 | 112 | 105 | 109 |
| 12 | 21 | 98 | 37 | 126 | 77 | 115 | 108 | 111 |

The invention claimed is:

1. An antiperspirant or deodorant composition comprising:
   i) an antiperspirant or deodorant active,
   ii) a liquid carrier for the antiperspirant or deodorant active, and
   iii) fragrance
   in which the fragrance comprises a mixture of first and second fragrances, respectively (iiia) and (iiib), the first fragrance (iiia) being free from encapsulation and comprising fragrance components having a boiling point of higher than 250° C. at 1 bar pressure in a weight proportion of greater than 65% and
   the second fragrance (iiib) being encapsulated in a water-insoluble shear-sensitive encapsulating material as shear sensitive capsules and comprising fragrance components having a boiling point of greater than 250° C. at 1 bar pressure in a weight proportion of less than 65%;
   wherein the water insoluble shear-sensitive encapsulating material comprises a water-insoluble gelatin coacervate and wherein the composition is anhydrous.

2. A composition according to claim 1 in which the first fragrance contains from 70 to 90% by weight of fragrance components having a boiling point of >250° C.

3. A composition according to claim 1 in which the second encapsulated fragrance contains from 35 to <65% of fragrance components having a boiling point of >250° C. and 15 to 35% by weight of fragrance components having a boiling point of ≤220° C.

4. A composition according to claim 1 in which the shear sensitive encapsulating material comprises a water-insoluble gelatin coacervate or an aminoplast.

5. A composition according to claim 4 in which the shear sensitive encapsulating material comprises a water-insoluble gelatin coacervate.

6. A composition according to claim 1 in which the shear sensitive capsules have a volume average particle diameter in the range of 25 to 70 μm, a shell having a measured thickness in the range of from 0.25 to 9 μm, a ratio of the shell thickness to the average particle diameter in the range of from 1:5 to 1 and a Hysitron hardness in the range of from 1.5 MPa to 50 MPa.

7. A composition according to claim 1 in which the combined weight of non-encapsulated fragrance and encapsulated fragrance is from 1 to 6% of the weight of the composition, excluding propellant.

8. A composition according to claim 1 in which the composition contains the non-encapsulated fragrance and the encapsulated fragrance in the weight ratio of from 1:5 to 10:1.

9. A composition according to claim 8 in which the non-encapsulated fragrance and the fragranced incorporated within the capsules are present in a weight ratio of from 1:1 to 3:1.

10. A composition according to claim 1 further comprising moisture-sensitive capsules.

11. A composition according to claim 10 in which the moisture-sensitive capsules and the shear-sensitive capsules are present in a weight ratio of from 3:1 to 1:20.

12. A composition according to claim 11 in which the moisture-sensitive capsules and the shear-sensitive capsules are present in a weight ratio of from 3:2 to 1:5.

13. A composition according to claim 1 in which the liquid carrier comprises a volatile silicone and optionally a non-volatile oil selected from esters between alkyl and aromatic compounds and ethers between polyalkylene oxide and an aliphatic alcohol.

14. A composition according to claim 13 in which the non-volatile oil comprises an alkyl benzoate or/and a polypropylene oxide of a C2-6 alkanol.

15. A composition according to claim 1 which is anhydrous.

16. A composition according to claim 1 in which the composition contains an aqueous phase, and the encapsulated fragrance is either free from moisture-sensitive capsules or if moisture sensitive capsules are present, the shear sensitive capsules are present in a weight ratio to the moisture sensitive capsules of at least 10:1.

17. An antiperspirant or deodorant product comprising a composition according to claim 1 in the form of an anhydrous stick contained within a dispensing container.

18. A method of masking body malodour over an extended period of time in which an antiperspirant or deodorant composition according to claim 1 is applied topically to axillary skin and left in place for a period of at least 4 hours.

* * * * *